United States Patent [19]
Ziemek

[11] 3,981,869
[45] Sept. 21, 1976

[54] PROCESS FOR THE PREPARATION OF HETEROCYCLIC COMPOUNDS

[75] Inventor: Peter Ziemek, Cologne, Germany

[73] Assignee: Bayer Aktiengesellschaft, Leverkusen, Germany

[22] Filed: Aug. 5, 1974

[21] Appl. No.: 494,911

[30] Foreign Application Priority Data
Aug. 10, 1973  Germany............................ 2340571

[52] U.S. Cl.......................... 260/240 G; 260/240.8; 260/240.9; 260/252; 260/256.4 F; 260/256.5 R; 260/294.8 D; 260/296 H; 260/302 F; 260/307 D; 260/309.2
[51] Int. Cl.²......................................... C09B 23/04
[58] Field of Search.......... 260/240 D, 240.9, 240.8, 260/240 G, 309.2, 302 F, 307 D, 294.8 D, 296 H, 256.4 F, 256.5 R, 252

[56]  References Cited
UNITED STATES PATENTS

| | | | |
|---|---|---|---|
| 2,504,617 | 4/1950 | Anish................... | 260/240.9 |
| 2,522,854 | 9/1950 | Brink et al........... | 260/309.2 |
| 2,710,823 | 6/1955 | Katz..................... | 260/240 G |
| 2,872,449 | 2/1959 | Baumann et al...... | 260/240 G |
| 3,401,048 | 9/1968 | Okubo et al.......... | 260/240.9 |
| 3,406,178 | 10/1968 | Crocker et al........ | 260/240 G |
| 3,417,082 | 12/1968 | Taylor.................. | 260/240 G |
| 3,586,694 | 6/1971 | Shen et al............ | 260/240 G |
| 3,769,279 | 10/1973 | Kuhlthau et al...... | 260/240 G |
| 3,795,680 | 3/1974 | Burton et al......... | 260/309.2 |

FOREIGN PATENTS OR APPLICATIONS
1,150,475  6/1963  Germany

OTHER PUBLICATIONS
Elderfield Heterocyclic Compounds vol. 5, 1957 John Wiley & Sons, N.Y., N.Y., pp. 419, 420, 421, 422, 440, 441, 506, 507.
Finar Organic Chemistry vol. 1, 1964 p. 152 Longmans, Green & Co., Ltd., London.

*Primary Examiner*—Arthur P. Demers
*Attorney, Agent, or Firm*—Plumley and Tyner

[57] ABSTRACT
Process for the preparation of heterocyclic compounds of the general formula

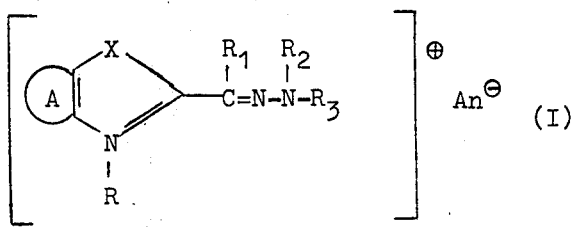

by condensation of an o-substituted amine of the general formula

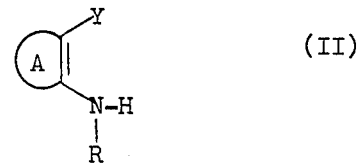

with a carbonyl compound of the general formula

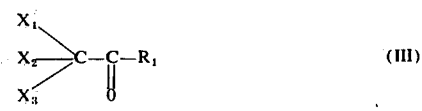

in the presence of a hydrazine of the general formula

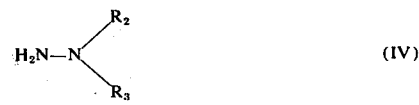

followed by quaternization if appropriate. In the formulae the radicals have the meaning as indicated below.

6 Claims, No Drawings

PROCESS FOR THE PREPARATION OF HETEROCYCLIC COMPOUNDS

The subject of the invention is a new process for the preparation of heterocyclic compounds of the general formula

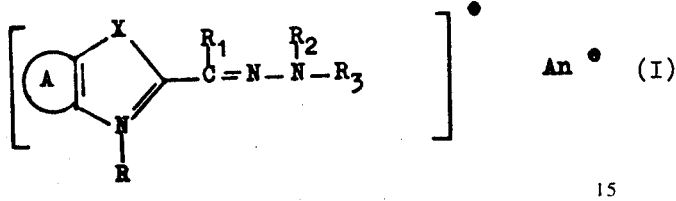

wherein
A denotes an aromatic-carbocyclic or aromatic-heterocyclic ring system,
X denotes O, S or N-$R_4$,
$R_4$ denotes hydrogen, alkyl, cycloalkyl, aralkyl or aryl,
R denotes hydrogen, alkyl, alkenyl, cycloalkyl, aralkyl or aryl,
$R_1$ denotes hydrogen or alkyl,
$R_2$ denotes hydrogen, alkyl, cycloalkyl, aralkyl or aryl,
$R_3$ denotes alkyl, cycloalkyl, aralkyl, aryl or a heterocyclic radical, or
$R_2$ and $R_3$ conjointly denote a constituent of a 5-membered or 6-membered heterocyclic ring system and
An $^\ominus$ denotes an anion
and wherein
the cyclic and acyclic radicals can carry non-ionic substituents by condensation of an o-substituted amine of the general formula

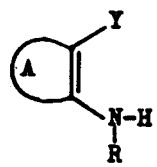

wherein
Y is X-H and
A, R and X have the indicated meaning with a carbonyl compound of the general formula

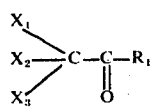

wherein
$R_1$ has the indicated meaning,
$X_1$ denotes hydroxyl, methoxy, ethoxy or halogen and
$X_2$ and $X_3$ denote halogen or conjointly denote oxygen in the presence of a hydrazine of the general formula

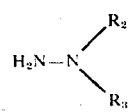

wherein
$R_2$ and $R_3$ have the indicated meaning followed by quaternisation if appropriate.

Examples of suitable rings A are the benzene, naphthalene, pyridine, pyrimidine or pyrazine ring.

Preferred rings A are aromatic-carbocyclic rings, especially benzene and naphthalene rings, which optionally carry non-ionic substituents.

The preparation of dyestuffs of the formula (I) in which
X denotes sulphur and
the ring A represents a benzene or naphthalene ring which is optionally substituted by non-ionic radicals should be singled out particularly.

Examples of non-ionic substituents of the ring A are halogen, such as chlorine and bromine, alkyl, especially $C_1$-$C_4$-alkyl, cycloalkyl, especially cyclohexyl, aryl, especially phenyl, alkoxy, especially $C_1$-$C_4$-alkoxy, nitro, nitrile, amino, acylamino, especially $C_1$-$C_4$-alkylcarbonylamino, and -sulphonylamino, alkylsulphonyl, especially $C_1$-$C_4$-alkylsulphonyl, arylsulphonyl, especially phenylsulphonyl or tolylsulphonyl, aralkylsulphonyl, such as benzylsulphonyl, hydroxyl, carboxyl, carboalkoxy, especially with 1 to 4 C atoms in the alkoxy group, carbonamide and sulphonamide.

The alkyl, cycloalkyl, aryl and aralkyl radicals of the formula (I) and those of the abovementioned substituents can contain further substituents, for example OH, CN, halogen, such as Cl or Br, nitro, carboxyl, methoxycarbonyl, ethoxycarbonyl, carbonamide, sulpho or sulphonamide.

The amino, sulphonamide and carbonamide groups can be monosubstituted and disubstituted at the nitrogen, for example by alkyl, especially $C_1$-$C_4$-alkyl, aryl, especially phenyl, and aralkyl, especially phenyl-$C_1$-$C_4$-alkyl, and the said substituents can be substituted further as indicated above.

By acylamino groups there are in particular understood alkylcarbonylamino, arylcarbonylamino, aralkylcarbonylamino, alkylsulphonylamino, arylsulphonylamino and aralkylsulphonylamino groups.

Within the scope of the present invention, alkyl is in general preferably to be understood as alkyl groups of 1 to 4 C atoms, cycloalkyl is preferably to be understood as cyclohexyl and aralkyl is preferably to be understood as benzyl and phenylethyl, whilst aryl preferably represents phenyl or naphthyl.

Particularly suitable radicals $R_2$ and $R_3$ are: $C_1$-$C_4$-alkyl, phenyl, which can be substituted by $C_1$-$C_4$-alkyl, $C_1$-$C_4$-alkoxy, nitro, halogen or $C_1$-$C_4$-dialkylamino, or benzyl. The radicals $R_2$ and $R_3$ conjointly with the nitrogen preferably form an indoline, carbazole or tetrahydroquinoline radical which can be substituted by $C_1$-$C_4$-alkyl, $C_1$-$C_4$-alkoxy or halogen.

Examples of heterocyclic radical $R_3$ are: benzthiazolyl-2, benzoxazolyl-2, benzimidazolyl-2, oxazolyl-2, triazolyl-2, thiazolyl-2, thiophenyl-2, purine-2, pyridine-2, pyrimidine-2, cinnolinyl-3, quinoxazinyl-2 or quinazolinyl-2.

Suitable substituents R are preferably: hydrogen, $C_1-C_4$-alkyl; alkyl, hydroxyethyl, cyanoethyl, carboxyethyl, methoxy- or ethoxy-carbonyl-methyl or -ethyl, allyl, benzyl or phenylethyl, whilst $R_1$ is preferably hydrogen or $C_1-C_4$-alkyl.

Examples of compounds of the general formula (II) are: o-phenylenediamine, 2-methylamino-aniline, 2-methylamino-4-chloroaniline, 2-methylamino-4-methoxyaniline, 2-methylamino-4-nitroaniline, 2-methylamino-4-methylsulphonylaniline, 2-aminophenol, 2-methylaminophenol, 2-benzylaminophenol, 2-amino-4-methylsulphonyl-phenol, 2-amino-4-nitrophenol, 2-methylamino-6-nitrophenol, 2-ethylamino-4-methoxyphenol, 2-methylamino-4-methyl-phenol, 2-amino-3,5-dichlorophenol, 2-amino-thiophenol, 2-methylamino-thiophenol, 2-benzylamino-thiophenol, 2-methylamino-4-chloro-thiophenol, 2-amino-4-methoxy-thiophenol, 2-ethylamino-4-nitrothiophenol, 2-methylamino-4-dimethylamino-thiophenol, 1-hydroxy-2-aminonaphthalene and 2-hydroxy-3-aminonaphthalene.

As examples of keto compounds (III) which can be employed preferentially there may be mentioned pyruvic acid, pyruvic acid esters, glyoxylic acid, glyoxylic acid esters, chloral, dichloroacetic acid and dichloroacetic acid esters, compounds of predominant interest being glyoxylic acid and its derivatives, such as chloral, dichloroacetic acid and glyoxylic acid esters.

As examples of representatives of the hydrazines (IV) there may be mentioned: phenylhydrazine, 1,1-dimethylhydrazine, 1-methyl-1-phenylhydrazine, 1-methyl-1-(4-methoxyphenyl)-hydrazine, 1-ethyl-1-(4-methylphenyl)-hydrazine, 1-methyl-1-(4-nitrophenyl)-hydrazine, 1,1-diphenyl-hydrazine, 1,1-di-p-tolyl-hydrazine, 1-methyl-1-benzimidazolyl-(2)-hydrazine, 1-methyl-1-pyridyl-(2)-hydrazine, N-amino-indoline and N-aminocarbazole.

The compounds of the general formula (I) can be prepared in the most diverse solvents. For example, it is possible to use aqueous hydrochloric acid, alcohols, toluene, chlorobenzene, chloroform, dimethylformamide or phosphorus oxychloride.

The reaction is preferably carried out by first reacting the hydrazine with the carbonyl compound at a lower temperature, preferably between $-15°$ and $30°C$. In some cases, the reaction product can be isolated at this stage. However, in most cases the o-disubstituted compound (II) is added without this intermediate isolation and the reaction mixture is stirred at higher temperatures, preferably at between $40°$ and $150°C$.

The dyestuff is isolated by simple filtration or by salting out with NaCl and is recrystallised if appropriate.

If a compound (II) with R = hydrogen is employed, it is possible, depending on the carbonyl compound and solvent employed, to isolate the hydrazone of the general formula

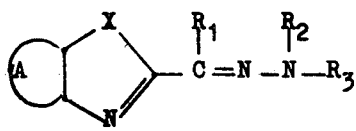

direct, or to prepare the hydrazone by stirring the reaction mixture with cold alkali, for example sodium carbonate solution. (V) can be isolated by extraction by shaking with, for example, toluene or chloroform. (V) can be quaternised to the compounds (I), in the reaction medium or after isolation and subsequent dissolution in solvents such as aromatic hydrocarbons or chlorinated hydrocarbons, by reaction with compounds of the general formula

In the formulae (V) and (VI)
A, X, R — with the exception of R = hydrogen —, $R_1$, $R_2$ and $R_3$ have the meaning indicated in the formula (I)
and
Z denotes a radical which can be split off as the anion $An^\ominus$ Examples of suitable quaternising agents (VI) are: alkyl halides and allyl halides, such as $C_1-C_4$-alkyl chloride, allyl chloride or allyl bromide, dialkyl sulphates, such as dimethyl sulphate or diethyl sulphate, benzenesulphonic or toluenesulphonic acid methyl esters or ethyl esters, benzyl chloride and also epoxides, such as ethylene oxide or epichlorohydrin, chloroacetic acid methyl ester or ethyl ester, β-chloropropionic acid and acrylic acid derivatives, such as acrylamide, acrylic acid methyl ester or ethyl ester or acrylonitrile.

The anions are determined by the process of preparation; however, they can be replaced by other anions in accordance with known processes. Both organic and inorganic anions can be used. Colourless anions are preferred. For dyeing from an aqueous medium, anions which do not excessively impair the solubility of the dyestuff in water are preferred. The anion is in general determined by the process of preparation and by the purification of the crude dyestuff which may have been carried out. In general, the dyestuffs are in the form of halides (especially chlorides or bromides) or of methosulphates, ethosulphates, sulphates, benzenesulphonates or toluenesulphonates, or of acetates. The anions can be replaced by other anions in a known manner.

Dyestuffs as obtained according to the invention are in part known, for example from DT-PS 1,083,000 and DT-PS 1,150,475. As compared to the processes of these patent specifications, the process according to the invention is distinguished by being technically particularly simple to carry out; for example, the process can be carried out as a one-pot process. A further advantage is the easy accessibility of the starting compounds, which in many cases are already being manufactured on an industrial scale, and in the available range of variation. Thus, for example, a large number of different hydrazones or hydrazone dyestuffs can be prepared from an o-disubstituted aromatic compound by choosing the most varied hydrazines of the general formula (IV).

EXAMPLE 1

7.3 g of chloral in 20 ml of ethanol are added dropwise over the course of 30 minutes to a solution of 6.1 g of α-methylphenylhydrazine, 5.5 g of o-aminothiophenol and 3 g of pyridine in 50 ml of ethanol at 20°C. The mixture is stirred for 30 minutes at 20°C and the temperature is then raised to the reflux temperature. After boiling for 2 hours, the reaction solution is allowed to cool and poured out into an aqueous sodium carbonate solution, and the mixture is extracted with benzene. The organic phase is dried and the solvent is stripped off. Yellowish crystals of the formula

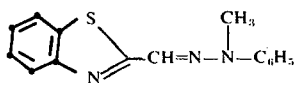

are obtained, which after recrystallisation from benzene/petroleum ether melt at 133 to 137°C.

EXAMPLE 2

Method A 1.4 g of the hydrazone prepared according to Example 1 are dissolved in 50 ml of chlorobenzene and 1 ml of dimethyl sulphate is added. The mixture is stirred for 3 hours at 120° to 130°C, whereupon the dyestuff of the formula

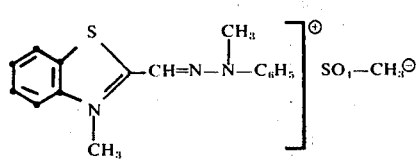

separates out in the form of red crystals. The mixture is cooled and the dyestuff is filtered off. The dyestuff dyes polyacrylonitrile and acid-modified polyester and polyamide fibres in very fast yellow shades.

Method B

The hydrazone from Example 1 is prepared from α-methylphenylhydrazine, o-aminothiophenol and chloral in chlorobenzene. After completion of the reaction, the cold chlorobenzene solution is washed with bicarbonate solution and with water, and is dried. Dimethyl sulphate is then added and the mixture is stirred for 5 hours at 110°C, the chlorobenzene is blown out with steam and the dyestuff is precipitated with NaCl.

with water and precipitation with NaCl. The dyestuff dyes polyacrylonitrile in yellow shades.

The same results are obtained with chlorobenzene and o-dichlorobenzene as solvents.

EXAMPLE 4

Methods 22.2 g of N-amino-2,3-dihydro-2-methyl-indole are mixed with 24.4 g of 50% strength glyoxylic acid and 200 ml of benzene and the mixture is boiled for 3 hours under a water separator. The brown solution is freed from benzene and the residue is recrystallised from toluene. 26 g of colourless crystals of melting point 142° to 146°C, of the formula

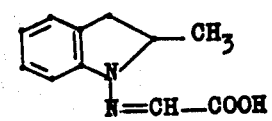

are obtained.

Method B 19.35 g of dichloroacetic acid are mixed with 37.4 g of morpholine and 22.2 g of N-amino-2,3-dihydro-2-methyl-indole in 500 ml of toluene at room temperature. The mixture is then stirred for 14 hours at 80°C, allowed to cool and extracted by shaking with water. The aqueous phase is then acidified with hydrochloric acid and the crystals which have precipitated are filtered off and dried.

The identity of the compound prepared according to A and B was confirmed by IR and mixed melting point.

EXAMPLE 5

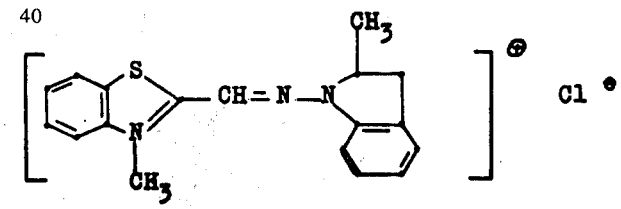

EXAMPLE 3

8.9 g of α-methyl-benzthiazolyl-(2)-hydrazine are dissolved in 50 ml of dimethylformamide. 7.3 g of chloral dissolved in 10 ml of dimethylformamide are added dropwise thereto at −10°C, the mixture is stirred for a further 15 minutes and 6.5 g of o-methylaminothiophenol, which has been diluted with 20 ml of dimethylformamide, are then added dropwise whilst stirring. The temperature is then raised to 120°C over the course of 60 minutes and the mixture is stirred for 2 hours at 120°C. Brownish crystals of the dyestuff of the formula

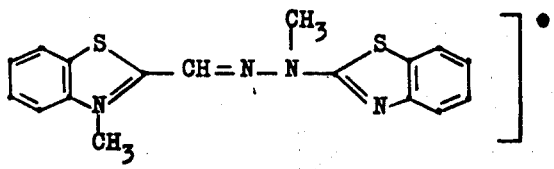

separate out and are filtered off after cooling. Further dyestuff is obtained from the mother liquor by dilution 10.2 g of the glyoxylic acid derivative prepared according to Example 4 are suspended in 100 ml of chlorobenzene, 30 ml of phosphorus oxychloride and 5 g of phosphorus pentoxide are added and the mixture is cooled to −10°C. 6.3 g of o-methylaminothiophenol in 50 ml of chlorobenzene are added dropwise to this mixture and the whole is stirred for a further 2 hours at 50°C, during which time brown crystals begin to separate out. The solvent is stripped off in a water pump vacuum and the residue is poured onto ice. The dyestuff is salted out with NaCl and recrystallised from hot water, after clarifying with active charcoal. The dyestuff dyes polyacrylonitrile in reddish-tinged yellow shades.

The following hydrazones can be prepared in accordance with the process of Example 1:

Examples 6 to 22

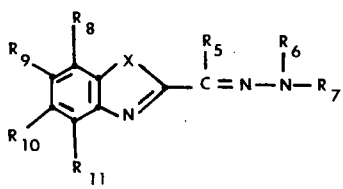

| X  | $R_8$ | $R_9$ | $R_{10}$ | $R_{11}$ | $R_5$ | $R_6$ | $R_7$ | Melting point |
|----|----|----|----|----|----|----|----|----|
| S  | H  | H  | H  | H  | H  | $CH_3$ | $C_6H_5$ | 133–137°C |
| S  | H  | H  | H  | H  | H  | $CH_3$ | $CH_3$ | 143°C |
| S  | H  | H  | H  | H  | H  | $C_6H_5$ | $C_6H_5$ | 141–144°C |
| S  | H  | H  | H  | H  | H  | $CH_3$ | p-$C_6H_4$—$OCH_3$ | 134.5–137°C |
| S  | H  | H  | H  | H  | H  | $CH_3$ | Benzthiazolyl(2) | 220–227°C |
| S  | H  | Cl | H  | H  | H  | 2,3-Dihydro-2-methylindolyl(1) | | 108–111°C |
| S  | H  | H  | H  | H  | H  | 2,3-Dihydro-2-methylindolyl(1) | | 148–151°C |
| NH | H  | H  | $NO_2$ | H  | H  | 2,3-Dihydro-2-methylindolyl(1) | | 128–132°C |
| O  | H  | H  | $NO_2$ | H  | H  | 2,3-Dihydro-2-methylindolyl(1) | | 195–198°C |
| O  | Cl | H  | Cl | H  | H  | 2,3-Dihydro-2-methylindolyl(1) | | 168–170°C |
| O  | Naphthalene | | | H  | H  | 2,3-Dihydro-2-methylindolyl(1) | | 203–204°C |
| O  | H  | H  | $C_2H_5$—$SO_2$— | H  | H  | 2,3-Dihydro-2-methylindolyl(1) | | 159–163°C |
| O  | H  | H  | H  | H  | H  | 2,3-Dihydro-2-methylindolyl(1) | | 113–115°C |
| O  | H  | H  | H  | H  | H  | $CH_3$ | p-$C_6H_4$—$OCH_3$ | 138–146°C |
| O  | H  | H  | H  | H  | H  | $C_6H_5$ | $C_6H_5$ | 145–152°C |
| O  | H  | H  | H  | H  | H  | $CH_3$ | $C_6H_5$ | 140°C |
| O  | H  | H  | H  | H  | H  | $CH_3$ | Benzthiazolyl(2) | 255–256°C |

The following dyestuffs can be prepared according to the process of Example 2:

Examples 23 to 40

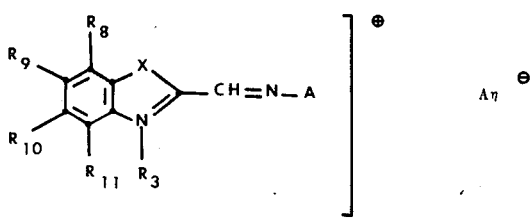

| X | $R_8$ | $R_9$ | $R_{10}$ | $R_{11}$ | $R_3$ | A | Colour shade on polyacrylonitrile |
|---|----|----|----|----|----|----|----|
| S | H | H | H | H | $CH_3$ | Phenylmethylamino | |
| S | H | $OCH_3$ | H | H | $CH_3$ | Phenylmethylamino | yellow |
| S | H | H | H | H | $CH_3$ | Diphenylamino | yellow |
| S | H | H | H | H | $CH_3$ | Methyl-p-anisidylamino | golden yellow |
| S | H | H | H | H | $CH_3$ | Carbazolyl(1) | golden yellow |
| S | H | $CH_3$ | H | H | $CH_3$ | 2-Methylindolinyl(1) | yellow |
| S | H | H | H | H | $C_6H_5CH_2$— | 2-Methylindolinyl(1) | yellow |
| S | H | H | H | H | $CH_3$ | 5-Methoxy-2,3,3-trimethyl-indolinyl(1) | orange |
| S | H | $NO_2$ | H | H | $CH_3$ | 5-Methoxy-2,3,3-trimethyl-indolinyl(1) | red |
| O | H | H | H | H | $CH_3$ | Methyl-phenyl-amino | yellow |
| O | H | H | H | H | $CH_3$ | 2-Methylindolinyl(1) | yellow |
| O | H | H | $C_2H_5$—$SO_2$ | H | $CH_3$ | 2-Methylindolinyl(1) | yellow |
| O | Cl | H | Cl | H | $CH_3$ | 2-Methylindolinyl(1) | yellow |
| O | H | H | $NO_2$ | H | $C_2H_5$ | 2-Methylindolinyl(1) | yellow |
| S | Cl | H | H | H | $CH_3$ | 2-Methylindolinyl(1) | yellow |
| S | H | H | $NO_2$ | H | $C_2H_5$ | 2-Methylindolinyl(1) | yellow |
| S | H | H | H | H | $C_6H_5CH_2$ | Tetrahydro quinoline(1) | yellow |

-continued

The following dyestuffs can be prepared according to the process of Example 2:
Examples 23 to 40

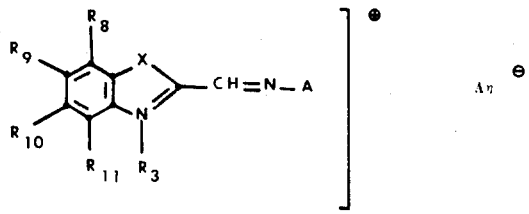

| X | $R_8$ | $R_9$ | $R_{10}$ | $R_{11}$ | $R_3$ | A | Colour shade on polyacrylonitrile |
|---|---|---|---|---|---|---|---|
| S | H | $C_6H_5CH_2-$ | H | H | $CH_3$ | Phenylmethylamino | yellow |

I claim:
1. Process for preparing compounds of the formula

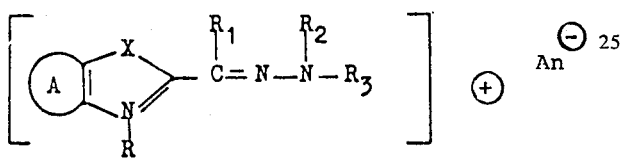

by condensing an amine of the formula

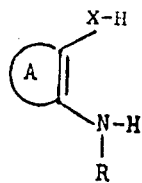

with a carbonyl compound of the formula

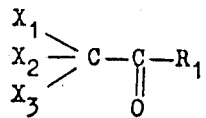

in the presence of a hydrazine of the formula

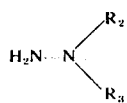

wherein
A is a benzene; naphthalene; pyridine; pyrimidine; or a pyrazine ring; or a benzene or naphthalene ring which is substituted with halogen, $C_1$-$C_4$-alkyl, cyclohexyl, phenyl, $C_1$-$C_4$-alkoxy, nitro, cyano, amino, $C_1$-$C_4$-alkyl-carbonylamino, $C_1$-$C_4$-alkyl-sulphonylamino, $C_1$-$C_4$-alkyl-sulphonyl, phenylsulphonyl, tolyl-sulphonyl, benzylsulphonyl, hydroxyl, carboxyl, carboalkoxy with 1 to 4 C atoms in the alkoxy group, carbonamide or sulphonamide;

X is O, S or N-$R_4$;
$R_4$ is hydrogen, $C_1$-$C_4$-alkyl; cyclohexyl; benzyl; phenethyl; phenyl or naphthyl;
$R_1$ is hydrogen or $C_1$-$C_4$-alkyl;
$R_2$ is hydrogen, $C_1$-$C_4$-alkyl; cyclohexyl; benzyl; phenethyl; phenyl; naphthyl; or phenyl substituted by $C_1$-$C_4$-alkyl, $C_1$-$C_4$-alkoxy, nitro, halogen, $C_1$-$C_4$-dialkylamino, or benzyl;
$R_3$ is hydrogen, $C_1$-$C_4$-alkyl; cyclohexyl; benzyl; phenethyl; phenyl; naphthyl; phenyl substituted by $C_1$-$C_4$-alkyl, $C_1$-$C_4$-alkoxy, nitro, halogen, $C_1$-$C_4$-dialkylamino, or benzyl; benzthiazolyl-2; benzoxazolyl-2; benzimidazolyl-2; oxazolyl-2; triazolyl-2; thiazolyl-2; thiophenyl-2; purine-2; pyridine-2; pyrimidine-2; cinnolinyl-3; quinoxazinyl-2; or quinazolinyl-2; or
$R_2$ and $R_3$ conjointly with the N atom form an indoline; carbazole or tetrahydroquinoline radical or one of the foregoing radicals substituted by $C_1$-$C_4$-alkyl, $C_1$-$C_4$-alkoxy or halogen;
R is hydrogen, $C_1$-$C_4$-alkyl; allyl; cyclohexyl; benzyl; phenethyl; phenyl or naphthyl;
An$^\ominus$ is an anion;
$X_1$ is hydroxyl, methoxy, ethoxy or halogen; and
$X_2$ and $X_3$ are halogen or conjointly are oxygen.

2. Process according to claim 1, characterised in that dyestuffs according to the formula I of claim 1 are prepared in which
A denotes a benzene ring and
X denotes sulphur.

3. Process according to claim 1, characterised in that glyoxylic acid or glyoxylic acid derivatives are employed as carbonyl compounds.

4. Process according to claim 1, characterised in that open-chain 1,1-substituted hydrazines are employed.

5. Process according to claim 1, characterised in that N-aminoheterocyclic compounds are employed as hydrazines.

6. Process according to claim 1, characterised in that the reaction is carried out as a one-pot reaction.

* * * * *